United States Patent
Tanaka et al.

(10) Patent No.: US 10,697,912 B2
(45) Date of Patent: Jun. 30, 2020

(54) GAS DETECTION METHOD AND GAS DETECTOR

(71) Applicant: Riken Keiki Co., Ltd., Tokyo (JP)

(72) Inventors: Yuki Tanaka, Tokyo (JP); Ryuji Asada, Tokyo (JP); Yoshikazu Shibasaki, Tokyo (JP); Shunsuke Takahashi, Tokyo (JP)

(73) Assignee: RIKEN KEIKI CO., LTD., Tokyo (JP)

( * ) Notice: Subject to any disclaimer, the term of this patent is extended or adjusted under 35 U.S.C. 154(b) by 205 days.

(21) Appl. No.: 16/036,449

(22) Filed: Jul. 16, 2018

(65) Prior Publication Data

US 2019/0025233 A1 Jan. 24, 2019

(30) Foreign Application Priority Data

Jul. 21, 2017 (JP) .................. 2017-141769

(51) Int. Cl.
  *G01N 25/18* (2006.01)
  *G01N 25/30* (2006.01)
  (Continued)

(52) U.S. Cl.
  CPC ............ *G01N 25/18* (2013.01); *G01N 25/30* (2013.01); *G01N 27/16* (2013.01); *G01N 33/007* (2013.01);
  (Continued)

(58) Field of Classification Search
  CPC ...... G01N 1/22; G01N 25/1838; G01N 27/16; G01N 33/00; G01N 33/007; G01N 33/0014; G01N 33/0031
  See application file for complete search history.

(56) References Cited

U.S. PATENT DOCUMENTS

| 4,542,640 A | 9/1985 | Clifford |
| 4,670,405 A | 6/1987 | Stetter et al. |

(Continued)

FOREIGN PATENT DOCUMENTS

| JP | 2006-194851 A | 7/2006 |
| JP | 2007-057295 A | 7/2006 |

(Continued)

OTHER PUBLICATIONS

Extended European Search Report dated Nov. 7, 2018 from the corresponding European Application No. 18184905.0.
(Continued)

*Primary Examiner* — Nguyen Q. Ha
(74) *Attorney, Agent, or Firm* — Lucas & Mercanti, LLP

(57) ABSTRACT

Provided are a gas detection method and a gas detector which have a high durability to silicone poisoning and is capable of detecting the type and the concentration of a target gas to be detected with certain accuracy even when the detector is used in an environment where a silicone compound exists. The gas detector employs a contact combustion-type gas sensor which includes two gas detection elements, each intermittently driven, and in which only one gas detection element is supplied with a gas through a silicone removal filter. Acquired in an energization duration of each of the gas detection elements are two or more pieces of output data by the one gas detection element and two or more pieces of output data by the other gas detection element, which constitutes output variation patterns for a test gas. The output variation patterns are contrasted to a reference output variation pattern of each of four largely divided types of reference gases of a paraffinic hydrocarbon gas, a solvent gas, a hydrogen gas, and an argon gas, with the reference output variation patterns being acquired in
(Continued)

advance, thereby identifying the type of the target gas being detected in the test gas.

12 Claims, 3 Drawing Sheets

(51) Int. Cl.
*G01N 27/16* (2006.01)
*G01N 33/00* (2006.01)

(52) U.S. Cl.
CPC ..... *G01N 33/0014* (2013.01); *G01N 33/0031* (2013.01)

(56) References Cited

U.S. PATENT DOCUMENTS 4,888,295 A * 12/1989 Zaromb ............. G01N 27/4045
436/161

2013/0276517 A1 * 10/2013 Takano ................... G01M 3/16
73/40.5 R

FOREIGN PATENT DOCUMENTS

| JP | 2006-234834 A | 9/2006 |
|----|---------------|--------|
| JP | 2006250569 A | 9/2006 |
| JP | 2016-223925 A | 7/2018 |

OTHER PUBLICATIONS

Gabriela Soreanu et al., "Approaches concerning siloxane removal from biogas—A review"; Canadian Biosystems Engineering, Jan. 1, 2011 (Jan. 1, 2011), p. 8 1, XP055516830.
Jai B. Lad, et al., "Adsorption of dimethyl 5,12 ether (DME) on zeolite molecular sieves", Chemical Engineering Journal, vol. 256, Jul. 9, 2014 (Jul. 9, 2014), pp. 335-345, XP05517609.

* cited by examiner (a)

(b)

(c)

(d)

(a)

(b)

(c)

(d)

GAS DETECTION METHOD AND GAS DETECTOR

CROSS REFERENCE TO RELATED APPLICATION

This application claims priority of Japanese Application No. 2017-141769 filed Jul. 21, 2017, application which is incorporated herein by reference.

TECHNICAL FIELD

The present invention relates to a gas detector which is provided with a contact combustion-type gas sensor and a gas detection method to be executed in the gas detector.

BACKGROUND ART

For example, a certain type of contact combustion-type gas sensor used to detect a flammable gas is configured to include a gas detection element with a gas sensitive part firmly fixed to the surface of a temperature-measuring resistor that generates heat when energized, where the gas sensitive part is formed by an oxidation catalyst carried on a carrier made of metal oxide sintered compact.

In such a contact combustion-type gas sensor, when a silicone compound or a poisonous substance such as hexamethyldisiloxane or silicone oil exists in the atmosphere of a space to be measured, the poisonous substance is adsorbed and accumulated on the surface of the oxidation catalyst (poisoning). This causes the performance (reactivity) of the oxidation catalyst to deteriorate and the detection sensitivity to gradually degrade.

In view of such a problem, for example, it is conceivable to dispose a silicone removal filter and thereby prevent the poisoning of the gas detection element. A gas sensor that is provided with such a silicone removal filter is disclosed, for example, in Patent Literature 1.

CITATION LIST

Patent Literature

Patent Literature 1: Japanese Patent Application Laid-Open No. 2006-250569

SUMMARY OF INVENTION

Technical Problem

However, in a gas sensor as mentioned above, since part of a target gas being detected, for example, a solvent gas may be removed by the silicone removal filter, the target gas to be detected cannot be properly detected. Then, from the output itself provided by the contact combustion-type gas sensor, the type of the target gas detected (the cause gas from which the output originated) cannot be identified.

The present invention has been made in view of the foregoing circumstances, and has as its object the provision of a gas detection method by which the type and the concentration of a target gas to be detected can be detected with certain accuracy even when a gas detector is used in an environment where a silicone compound or a poisonous substance exists.

The present invention also has as its object the provision of a gas detector which has a high durability to silicone poisoning and is capable of detecting, with certain accuracy, the type and the concentration of a target gas to be detected.

A gas detection method of the present invention is executed in a gas detector that includes a contact combustion-type gas sensor in which two gas detection elements that each have a catalyst carried by a carrier made of a metal oxide sintered compact firmly fixed to a temperature-measuring resistor are intermittently driven to repeat a gas detection cycle that includes the same or continuous energization duration and a non-energization duration.

The gas detection method includes: supplying a reference gas having a known concentration of a target gas to be detected to one gas detection element through a silicone removal filter, and supplying the reference gas to the other gas detection element not through the silicone removal filter so as to acquire, in advance, a reference output variation pattern that is constituted by two or more pieces of output data acquired by the one gas detection element and two or more pieces of output data acquired by the other gas detection element in one gas detection cycle;

acquiring an output variation pattern which is constituted by two or more pieces of output data acquired by the one gas detection element for a test gas and two or more pieces of output data acquired by the other gas detection element for the test gas in one gas detection cycle; and performing a gas identification process in which the output variation pattern is contrasted to the reference output variation pattern to thereby identify a type of the target gas being detected in the test gas.

The gas detection method of the present invention is configured such that in the gas identification process, the type of the target gas being detected in the test gas is identified as any of types of a paraffinic hydrocarbon gas, a solvent gas, a hydrogen gas, and an argon gas.

Still furthermore, the gas detection method of the present invention may preferably be configured such that after the type of the target gas being detected in the test gas is identified in the gas identification process, first concentration datum is acquired on the basis of output data on the reference gas of the identified gas type and output data by the one gas detection element in the output variation pattern acquired for the test gas, and second concentration datum is acquired on the basis of the output data on the reference gas and output data by the other gas detection element in the output variation pattern acquired for the test gas; and the higher one of values represented by the first concentration datum and the second concentration datum is outputted as the concentration indication value of the target gas being detected.

The gas detection method of the present invention may preferably be configured such that the silicone removal filter of the contact combustion-type gas sensor is a filter including a support having air permeability, and silica carried by the support, the filter being subjected to an adsorption acceleration treatment by iron (III) chloride to accelerate adsorption of a silicone compound; or a filter including a support having air permeability and fumed silica carried by the support.

A gas detector of the present invention includes:

a contact combustion-type gas sensor, in which two gas detection elements are each disposed in each of two detection chambers that are partitioned from each other, and a gas inlet of one detection chamber is provided with a silicone removal filter, the gas detection elements each having a catalyst carried by a carrier made of a metal oxide sintered compact firmly fixed to a temperature-measuring resistor;

a sensor drive unit configured to intermittently drive each of the two gas detection elements so as to repeat a gas detection cycle that includes the same or continuous energization duration and a non-energization duration for each of the two gas detection elements;

an output processing unit configured to process output data from each of the two gas detection elements; and a display unit configured to display a type and a concentration of the target gas detected, wherein the output processing unit has a gas identification function to identify the type of the target gas being detected in the test gas by contrasting an output variation pattern to a reference output variation pattern acquired in advance for a reference gas having a known concentration of the target gas to be detected, the output variation pattern being constituted by two or more pieces of output data acquired by the one gas detection element for the test gas and two or more pieces of output data acquired by the other gas detection element for the test gas in one gas detection cycle.

The gas detector of the present invention may preferably be configured such that the target gas to be detected which is to be identified is a paraffinic hydrocarbon gas, a solvent gas, a hydrogen gas, and an argon gas.

Still furthermore, the gas detector of the present invention may preferably be configured such that the output processing unit further has one or both of functions (1) and (2) below.

(1) The function to acquire, after the type of the target gas being detected in the test gas is identified, first concentration datum on the basis of output data on the reference gas of the identified gas type and output data by the one gas detection element in an output variation pattern acquired for the test gas; to acquire second concentration datum on the basis of output data on the reference gas and output data by the other gas detection element in the output variation pattern acquired for the test gas; and to output the higher one of values represented by the first concentration datum and the second concentration datum as a concentration indication value of the target gas being detected to the display unit in conjunction with the gas type of the target gas being detected.

(2) The function to output as "another gas" the type of the target gas being detected to the display unit when an output variation pattern acquired for the test gas belongs to none of the target gases to be detected of which patterns were acquired in advance and which are to be identified; to acquire first concentration datum on the basis of output data on a reference gas of a reference output variation pattern of which output data variation tendency is relatively closer to that of an output variation pattern acquired for the test gas and output data by the one gas detection element in an output variation pattern acquired for the test gas; to acquire second concentration datum on the basis of output data on the reference gas and output data by the other gas detection element in the output variation pattern acquired for the test gas; and to output, to the display unit, the higher one of values represented by the first concentration datum and the second concentration datum as the concentration indication value of the another gas.

Furthermore, the gas detector of the present invention may preferably be configured such that each of the gas detection elements of the contact combustion-type gas sensor employs $ZrO_2$ or $Al_2O_3$ as the carrier and at least one type selected from the group consisting of Pt, Pd, PtO, $PtO_2$, and PdO as the catalyst.

The gas detector of the present invention may preferably be configured such that the silicone removal filter of the contact combustion-type gas sensor is a filter including a support having air permeability, and silica carried by the support, the filter being subjected to an adsorption acceleration treatment by iron (III) chloride to accelerate adsorption of a silicone compound; or a filter including a support having air permeability and fumed silica carried by the support.

Advantageous Effects of Invention

According to the gas detection method and the gas detector of the present invention, even when the gas detector is used in an environment where a silicone compound or a poisonous substance exists, it is possible to acquire highly reliable output for a target gas to be detected by at least one of the gas detection elements and also to provide a high durability to silicone poisoning.

Then, the output variation patterns that include output data groups, say, in one set of two or more pieces of output data acquired by each of the two gas detection elements in one gas detection cycle (four or more pieces of output data in total) are different from each other and unique to the type of a target gas to be detected, for example, to each of four type groups of a paraffinic hydrocarbon gas, a solvent gas, a hydrogen gas, and an argon gas. Furthermore, even when the gas detection element is poisoned (silicone poisoning), the output variation pattern of each gas will never be significantly varied. Thus, according to the gas detection method and the gas detector of the present invention, the type of a target gas being detected can be identified with certain accuracy by contrasting the output variation pattern acquired for the test gas to the reference output variation pattern acquired in advance.

Still furthermore, in the gas detection method and the gas detector of the present invention, first concentration datum is acquired on the basis of output data on the reference gas of the identified gas type and output data by one gas detection element in an output variation pattern acquired for a test gas; second concentration datum is acquired on the basis of output data on the reference gas and output data by the other gas detection element in an output variation pattern acquired for the test gas; and a value of the higher one of these pieces of data is outputted as a concentration indication value of the target gas being detected. According to the gas detection method and the gas detector of the present invention, this also makes it possible to detect, with certain accuracy, the concentration of the target gas to be detected having an identified type.

DESCRIPTION OF EMBODIMENTS

An embodiment of the present invention will be described in more detail below.

Gas Detection Method:

A gas detection method of the present invention is characterized by performing a gas identification process of identifying the type of a target gas being detected which is contained in a test gas, in which the target gas to be detected is, for example, a paraffinic hydrocarbon gas, a solvent gas, a hydrogen gas, and an argon gas.

The gas identification process is performed by contrasting the output variation pattern of a test gas acquired by a contact combustion-type gas sensor to a reference output variation pattern acquired in advance for a reference gas having a known concentration of a target gas to be detected.

The contact combustion-type gas sensor to be employed may be configured to include two gas detection elements, each having a catalyst carried by a carrier made of a metal oxide sintered compact firmly fixed to each temperature-measuring resistor. For example, a common test gas is supplied to one gas detection element through a silicone removal filter, whereas being supplied to the other gas detection element through no silicone removal filter. The structure of the gas detection element and the silicone removal filter will be discussed later.

Figure 1:
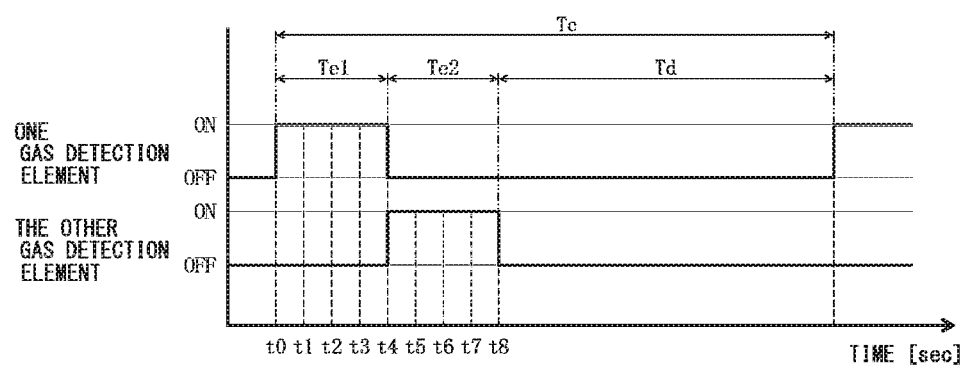
FIG. 1 is a timing chart showing an example drive scheme of a contact combustion-type gas sensor.

In the gas detection method of the present invention, it is preferable to intermittently drive each of the two gas detection elements in the contact combustion-type gas sensor so as to repeat a gas detection cycle that includes the same or continuous energization duration and non-energization duration for each of the two gas detection element. More specifically, in the gas detection method of the present invention, each of the two gas detection elements may be energized either at the same time or alternately. For example, as illustrated in FIG. 1, each gas detection element may preferably be intermittently driven so as to repeat a gas detection cycle Tc in which the two gas detection elements are alternately energized and which includes continuous energization durations Te1, Te2 and non-energization duration Td.

For example, as an operational condition of the contact combustion-type gas sensor, the voltage applied to each gas detection element may preferably have a magnitude within the range of 0.50 to 1.20 V, more preferably 1.0 V. Furthermore, for example, the energization durations (energization periods of time) Te1, Te2 for the respective gas detection elements are preferably 0.5 to 2 seconds, more preferably, one second. For example, the non-energization duration (non-energization period of time) Td is preferably one second or greater, more preferably, 3 seconds.

According to the drive scheme for such a contact combustion-type gas sensor, it is possible to reduce the power consumption of the gas detector, and since the de-energization period of time of the gas detection element is short, stable output can be provided without warming up the gas detection element for an extended period of time. In particular, when the two gas detection elements are alternately energized, a common power source circuit (not illustrated) can be used to drive both the gas detection elements. Thus, it is possible to reduce the power consumption of the gas detector.

The reference output variation pattern for a reference gas to be used in the gas identification process is acquired as follows.

In the energization durations Te1, Te2 for the respective gas detection elements in one gas detection cycle, gas detection signals from each gas detection element provided by acting the reference gas thereon are sampled, for example, at predetermined time intervals, thereby acquiring two or more pieces of output data for each gas detection element. Then, a data group with four or more pieces of acquired output data taken as one set is acquired as the reference output variation pattern. The number of pieces of output data forming the reference output variation pattern is not limited to a particular one; however, from the viewpoint of reliability of the gas identification process, the reference output variation pattern may preferably be constituted by three or more pieces of output data for each gas detection element (six or more in total).

The reference output variation pattern is acquired for each of four types of reference gases that are largely divided into the aforementioned paraffinic hydrocarbon gas, solvent gas, hydrogen gas, and argon gas.

The paraffinic hydrocarbon gas specifically has a carbon number of 1 to 6, and the reference output variation patterns of these gases indicate a mutually similar tendency. Thus, in the present invention, the gases are divided into the same gas type. Furthermore, likewise, as for the solvent gas, the reference output variation patterns for alcohols such as isopropyl alcohol, ketones such as acetone, aromatic hydrocarbons such as toluene, and other solvent gases indicate a mutually similar tendency. Thus, in the present invention, the gases are divided into the same gas type.

Figure 2:
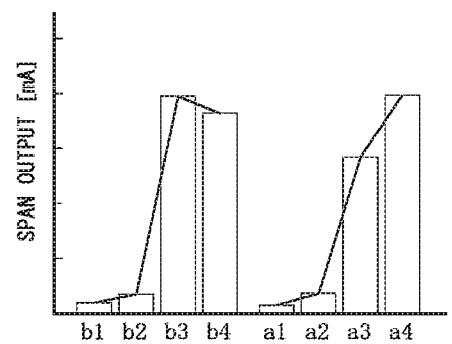
FIG. 2 is a conceptual diagram showing an example of a reference output variation pattern acquired for a reference gas of each of (a) a paraffinic hydrocarbon gas, (b) a solvent gas, (c) a hydrogen gas, and (d) an argon gas.
Figure 2:
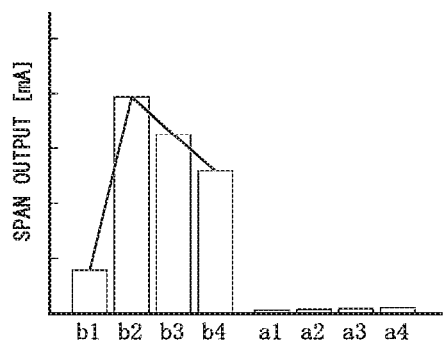
Figure 2:
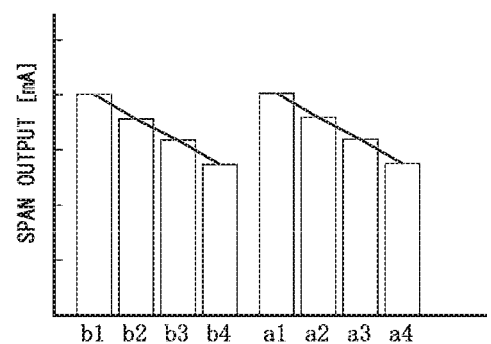
Figure 2:
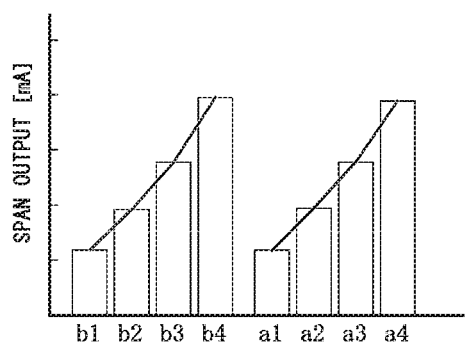

FIG. 2 is a conceptual diagram illustrating an example of reference output variation patterns. FIG. 2($a$) is a view illustrating the reference output variation pattern for the paraffinic hydrocarbon gas, (b) a view illustrating the reference output variation pattern for the solvent gas, (c) a view illustrating the reference output variation pattern for the hydrogen gas, and (d) a view illustrating the reference output variation pattern for the argon gas.

These reference output variation patterns were acquired by sampling gas detection signals at time intervals of 0.25 seconds (at points in time t1 to t8 in FIG. 1), the gas detection signals being provided by each of the two gas detection elements in one energization duration, for example, in one second for each gas detection element when the contact combustion-type gas sensor is driven, for example, by the drive scheme illustrated in FIG. 1.

The vertical axis of FIGS. 2($a$) to ($d$) represents the span output value that is provided by subtracting, from an output value acquired by sampling for the reference gas, an output value acquired by sampling in the same manner when air was introduced. Furthermore, a1 to a4 represent output data by one gas detection element to which a reference gas or air was supplied through a silicone removal filter, whereas b1 to b4 represent output data by the other gas detection element to which the reference gas or air was supplied not through the silicone removal filter.

As illustrated in FIG. 2($a$), for example, since the paraffinic hydrocarbon gas such as methane transmits through the silicone removal filter, the two gas detection elements provide output data a1 to a4, and b1 to b4 of span output values at a sufficiently high level, respectively. That is, the paraffinic hydrocarbon gas is detected by both the one gas detection element and the other gas detection element. For the reference output variation pattern of the paraffinic hydrocarbon gas, both the one gas detection element and the other gas detection element show the tendency (rapid increase variation tendency) that the span output values are low at the early stage of the energization duration but the span output values are varied by rapidly increasing at the later stage.

On the other hand, as illustrated in FIG. 2(b), since the solvent gas including aromatic hydrocarbons such as toluene, alcohols, and ketones is removed by the silicone removal filter, the span output values of the output data a1 to a4 by one gas detection element are substantially "0" and the other gas detection element provides the output data b1 to b4 of span output values at a sufficiently high level. That is, the solvent gas is substantially detected not by the one gas detection element but detected only by the other gas detection element. Then, the reference output variation pattern of the solvent gas shows the tendency (mountain type variation tendency) that the span output values are once increased with time for the other gas detection element, and then, the span output values are reduced with time.

Still furthermore, as illustrated in FIG. 2(c), since the hydrogen gas transmits through the silicone removal filter, the one gas detection element and the other gas detection element provide the output data a1 to a4, and b1 to b4 of span output values at a sufficiently high level, respectively. That is, the hydrogen gas is detected by both the one gas detection element and the other gas detection element. Then, for both the one gas detection element and the other gas detection element, the reference output variation pattern of the hydrogen gas shows the tendency (gradual decrease variation tendency) that the span output values are reduced with time.

Still furthermore, as illustrated in FIG. 2(d), since the argon gas transmits through the silicone removal filter, the one gas detection element and the other gas detection element provide the output data a1 to a4, and b1 to b4 of span output values at a sufficiently high level, respectively. That is, the argon gas is detected by both the one gas detection element and the other gas detection element. Then, for both the one gas detection element and the other gas detection element, the reference output variation pattern of the argon gas shows the tendency (gradual increase variation tendency) that the span output values are increased with time.

Figure 3:
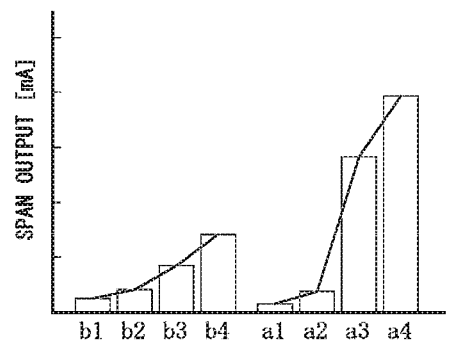
FIG. 3 is a conceptual diagram illustrating an example of an output variation pattern acquired for the reference gas of each of (a) the paraffinic hydrocarbon gas, (b) the solvent gas, (c) the hydrogen gas, and (d) the argon gas when exposed for a predetermined period of time to an environment in which a silicone compound exists.
Figure 3:
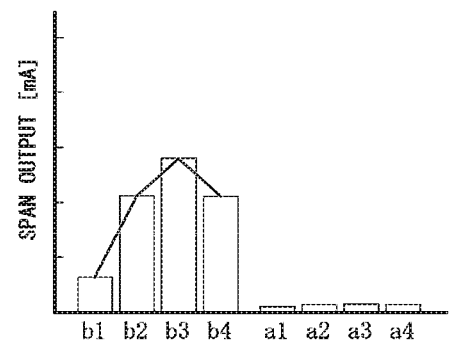
Figure 3:
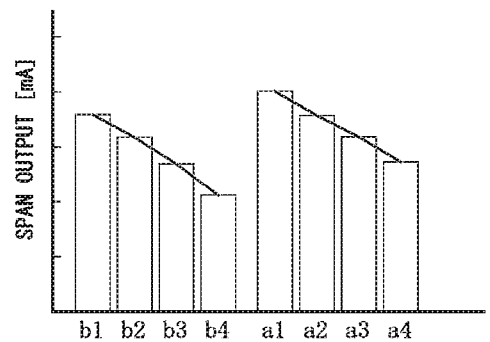
Figure 3:
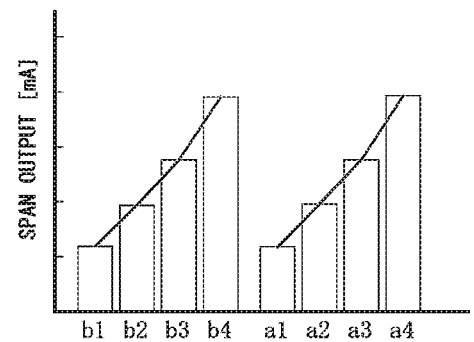

As described above, in the contact combustion-type gas sensor, the silicone compound or a poisonous substance is adsorbed and accumulated on the surface of the oxidation catalyst (poisoning), thereby causing the detection sensitivity to be gradually degraded. However, the output variation patterns constituted by four or more data groups that include two or more pieces of output data by the one gas detection element and two or more pieces of output data by the other gas detection element were found to be basically the same because the forms of the output variation patterns do not vary, for example, even if the silicone poisoning causes the magnitude of output from the gas detection element itself to be reduced. FIG. 3 is a conceptual diagram illustrating an example of output variation patterns acquired for the reference gas of each of (a) the paraffinic hydrocarbon gas, (b) the solvent gas, (c) the hydrogen gas, and (d) the argon gas when exposed for a predetermined period of time to an environment in which a silicone compound exists.

For example, as illustrated in FIG. 3(a), for both the one gas detection element and the other gas detection element, the output variation patterns for the paraffinic hydrocarbon gas such as methane show the tendency that though the magnitudes of the span output value themselves are reduced, the output values are low at the early stage of the energization duration and the output values are rapidly increased at the later stage.

Furthermore, as illustrated in FIG. 3(b), the output variation patterns of the solvent gas, for example, aromatic hydrocarbons such as toluene, alcohols, and ketones show the tendency (mountain type variation tendency) that the span output values according to the other gas detection element to which a gas is supplied not through the silicone removal filter are once increased with time, and then the span output values are reduced with time.

Still furthermore, as illustrated in FIG. 3(c), for both the one gas detection element and the other gas detection element, the output variation patterns of the hydrogen gas show the tendency (gradual decrease variation tendency) that the span output values are reduced with time.

Still furthermore, as illustrated in FIG. 3(d), for both the one gas detection element and the other gas detection element, the output variation patterns of the argon gas show the tendency (gradual increase variation tendency) that the span output values are increased with time.

As described above, the output variation patterns constituted by the four or more data groups that are acquired by each of the two gas detection elements are different from each other and unique depending on the type of a target gas to be detected (cause gas), that is, unique to each of the four types of the paraffinic hydrocarbon gas, the solvent gas, the hydrogen gas, and the argon gas. Furthermore, the form of an output variation pattern does not vary and basically the same, for example, even if the silicone poisoning causes the magnitude of output from a gas detection element itself to be reduced.

Thus, the gas detection method of the present invention enables identifying the type of a target gas being detected in a test gas by performing the gas identification process of determining the gas type of the form of a reference gas output variation pattern which the form of an output variation pattern (variation tendency) of the test gas acquired by the contact combustion-type gas sensor coincides with or is similar to.

By way of example, a description will be made to a method of determining an output variation pattern acquired for a test gas, in which for example, as the reference output variation patterns illustrated in FIG. 2, an output variation pattern acquired for a test gas is constituted by eight data groups that include four pieces of output data a1 to a4 sequentially acquired by the one gas detection element and four pieces of output data b1 to b4 sequentially acquired by the other gas detection element. Furthermore, let the span output values of the four pieces of output data a1 to a4 acquired by the one gas detection element be Ra1 to Ra4, respectively, and the span output values of the four pieces of output data b1 to b4 acquired by the other gas detection element be Rb1 to Rb4, respectively.

The output variation pattern acquired for a test gas is determined, for example, by sequentially performing the determination processes (1) to (4) shown below.

(1) Process of determining whether a target gas being detected in the test gas is a paraffinic hydrocarbon gas;

(2) Process of determining whether the target gas being detected is a solvent gas;

(3) Process of determining whether the target gas being detected is a hydrogen gas; and (4) Process of determining whether the target gas being detected is an argon gas.

(1) Process of Determining Whether the Target Gas being Detected in the Test Gas is a Paraffinic Hydrocarbon Gas.

In this determination process, for the output data a1 to a4 by the one gas detection element in the output variation pattern acquired for the test gas, the target gas being detected is identified to be a "paraffinic hydrocarbon gas" when the output variation pattern determination formula (1) below is satisfied. This output variation pattern determination formula (1) is a mathematical expression of "the rapid increase variation tendency" mentioned above in the reference output variation pattern of the paraffinic hydrocarbon gas.

$Ra4>Ra1$ and
$Ra1/Ra4<0.2$   Output variation pattern determination formula (1):

(2) Process of Determining Whether the Target Gas being Detected in the Test Gas is a Solvent Gas.

This determination process is performed when it is confirmed in the determination process (1) above that the target gas being detected in the test gas is not a paraffinic hydrocarbon gas.

In this determination process, for the output data a1 to a4 by the one gas detection element and the output data b1 to b4 by the other gas detection element in the output variation patterns acquired for the test gas, the target gas being detected is identified to be "a solvent gas" when the output variation pattern determination formula (2) below is satisfied. This output variation pattern determination formula (2) is a mathematical expression of "the mountain type variation tendency" mentioned above in the reference output variation pattern for the solvent gas.

$Ra4/Rb4<0.2$   Output variation pattern determination formula (2):

(3) Process of Determining Whether the Target Gas being Detected in the Test Gas is a Hydrogen Gas.

This determination process is performed when it is confirmed in the determination process (2) above that the target gas being detected in the test gas is neither a paraffinic hydrocarbon gas nor a solvent gas.

In this determination process, for the output data a1 to a4 by the one gas detection element and the output data b1 to b4 by the other gas detection element in the output variation patterns acquired for the test gas, the target gas being detected is identified to be a "hydrogen gas" when the output variation pattern determination formula (3) below is satisfied. This output variation pattern determination formula (3) is a mathematical expression of "the gradual decrease variation tendency" above in the reference output variation pattern for a hydrogen gas.

$Ra2>Ra3>$
$Ra4$ and
$Rb2>Rb3>$
$Rb4$   Output variation pattern determination formula (3):

(4) Process of Determining Whether the Target Gas being Detected in the Test Gas is an Argon Gas:

This determination process is performed when it is confirmed in the determination process (3) above that the target gas being detected in the test gas is not one of a paraffinic hydrocarbon gas, a solvent gas, and a hydrogen gas.

In this determination process, for the output data a1 to a4 by the one gas detection element and the output data b1 to b4 by the other gas detection element in the output variation patterns acquired for the test gas, the target gas being detected is identified to be an "argon gas" when all the output variation pattern determination formulas (4a) to (4d) below are satisfied. The output variation pattern determination formulas (4a) to (4d) are a mathematical expression of "the gradual increase variation tendency" mentioned above in the reference output variation pattern for an argon gas.

$Ra1<Ra2<$
$Ra3<Ra4$   Output variation pattern determination formula (4a):

$Rb1<Rb2<$
$Rb3<Rb4$   Output variation pattern determination formula (4b):

$Ra1/Ra4>0.2$   Output variation pattern determination formula (4c):

$Ra4/Rb4>0.5$   Output variation pattern determination formula (4d):

When it is confirmed in the determination processes (1) to (4) above that the target gas being detected in the test gas is not any one of a paraffinic hydrocarbon gas, a solvent gas, a hydrogen gas, and an argon gas, for example, the test gas is identified to be "another gas" such as a mixture gas of a plurality of target gases to be detected that are the same as or different from each other or a gas different in the type of base gas from the reference gas mentioned above.

Then, in the gas detection method of the present invention, the type of the target gas being detected in the test gas is identified, and then a gas concentration computation process of computing the concentration of the target gas being detected is performed.

In the gas concentration computation process, when it is identified in the gas identification process that the type of the target gas to be detected in the test gas is one of the four largely divided types of, i.e., a paraffinic hydrocarbon gas, a solvent gas, a hydrogen gas, and an argon gas which are to be identified as mentioned above, first concentration datum is acquired on the basis of the output data on the reference gas for the type of a gas identified and the output data acquired by the one gas detection element for the test gas. On the other hand, second concentration datum is acquired on the basis of the output data on the reference gas and the output data acquired by the other gas detection element for the test gas.

Here, the output data on the reference gas to be used when the concentration data is acquired is the one that is temporally latest in the reference output variation pattern. Referring to FIG. 2, the paraffinic hydrocarbon gas and the hydrogen gas employ the span output value of output data a4 by the one gas detection element; the solvent gas employs the span output value of the output data b4 by the other gas detection element; and the argon gas employs the higher one of the span output value of the output data a4 by the one gas detection element and the span output value of the output data b4 by the other gas detection element. Furthermore, likewise, for the output data acquired for the test gas, employed is each piece of output data by the two gas detection elements which is acquired to be temporally latest in the output variation pattern when acquiring concentration data.

On the other hand, when the test gas is identified to be "another gas" in the gas identification step, first concentration datum is acquired on the basis of the following: the output data (the span output value) on the reference gas of a reference output variation pattern which shows the output data variation tendency that is relatively close to that of the output variation pattern acquired for the test gas; and the span output value of the output data that is acquired to be temporally latest by the one gas detection element in the output variation pattern acquired for the test gas. Furthermore, second concentration datum is acquired on the basis of the output data (the span output value) on the reference gas and the span output value of the output data acquired to be temporally latest by the other gas detection element for the test gas.

Then, a value of the higher one of the concentration data according to the two gas detection elements is outputted to the display unit, in conjunction with an identified gas type, as the concentration indication value of the target gas to be detected having an identified gas type.

A description will next be given of a gas detector in which the aforementioned gas detection method is executed.

The gas detector of the present invention may be configured either as a portable type or a stationary type; however, as will be discussed later, since the gas detector of the present invention can be configured as one of which power consumption has been reduced, the gas detector of the present invention will be useful when configured as a portable type that operates on a battery.

The gas detector of the present invention is provided with a contact combustion-type gas sensor, a sensor drive unit configured to drive the contact combustion-type gas sensor, an output processing unit configured to process a gas detection signal from the contact combustion-type gas sensor, and a display unit configured to display the type of a target gas detected and the concentration thereof. The gas detector may also be configured to include an alarm unit configured to issue an alarm when the concentration of the target gas being detected has exceeded a reference value (alarm point) that is set for the target gas to be detected.

Figure 4:
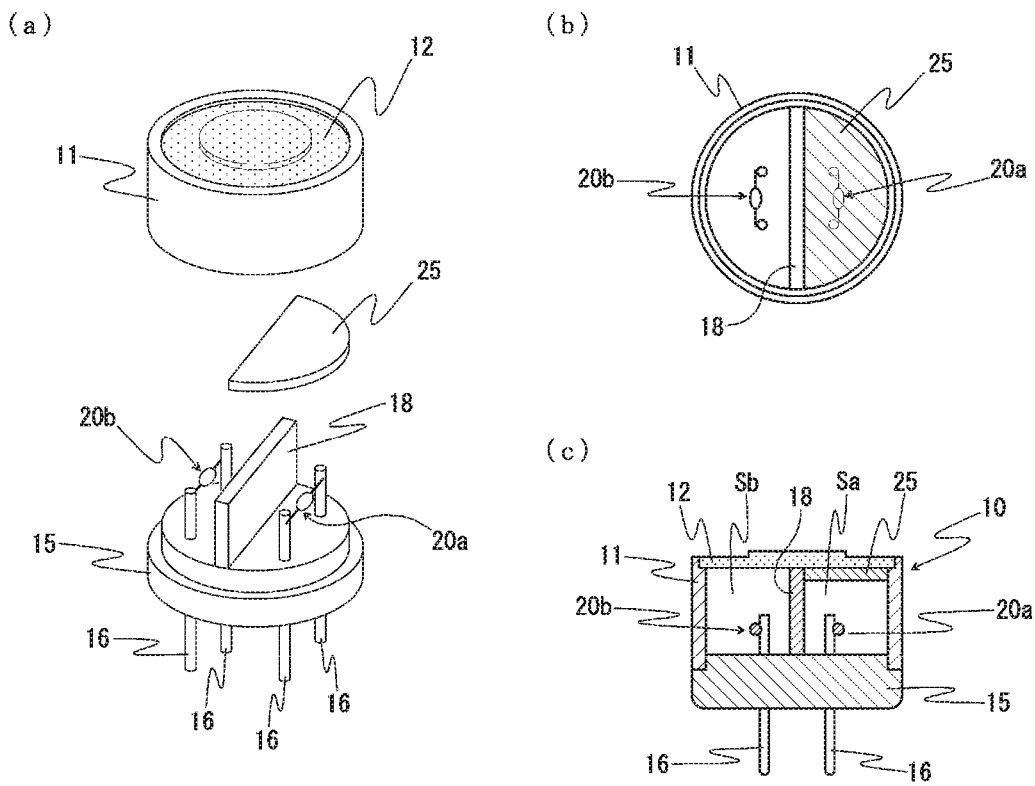
FIG. 4 illustrates an example structure of a contact combustion-type gas sensor to be used in a gas detector of the present invention; (a) an exploded perspective view, (b) a plan view with part of the structure not illustrated, and (c) a cross-sectional view.

FIG. 4 illustrates an example structure of a contact combustion-type gas sensor to be used in a gas detector of the present invention; (a) an exploded perspective view, (b) a plan view with part of the structure not shown, and (c) a cross-sectional view.

The contact combustion-type gas sensor 10 is provided with a case 11 in which formed are two detection chambers Sa, Sb that are partitioned by a partitioning plate 18 serving also as a heat shielding plate; and two gas detection elements 20a, 20b which are disposed in the two detection chambers Sa, Sb, respectively.

The case 11 has one end side opening which is blocked by an anti-inflammatory filter 12 made of, for example, a metal sintered compact and which is, for example, cylindrical in shape, and has the other end side opening which is provided with a base member 15 for supporting the gas detection elements 20a, 20b so as to tightly block the other end side opening.

On one surface of the base member 15 is provided the flat partitioning plate 18 that divides the inner space of the case 11 into two halves, and the gas detection elements 20a, 20b are disposed on both sides that sandwich the partitioning plate 18, respectively. Each of the gas detection elements 20a, 20b has the ends secured to the top portions of leads 16, respectively, for example, in an attitude that extends horizontally along the partitioning plate 18. Each of the leads 16 is provided so as to tightly penetrate the base member 15 and protrude and extend outwardly in the axial direction.

Figure 5:
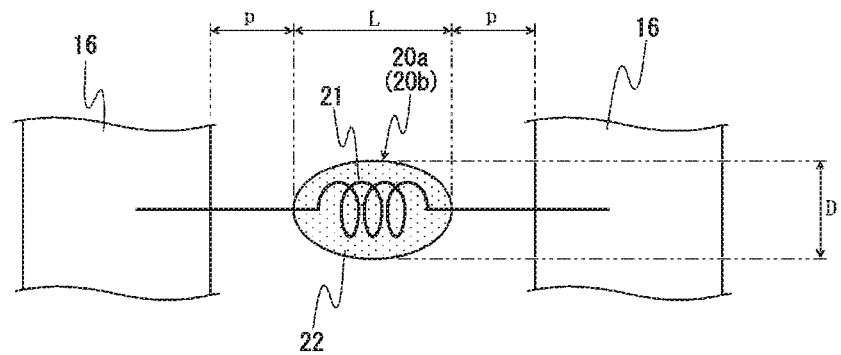
FIG. 5 is a cross-sectional view schematically illustrating the structure of an example of a gas detection element.

As illustrated in FIG. 5, each of the gas detection elements 20a, 20b is configured from a temperature-measuring resistor 21 which is energized to generate heat and a gas sensitive part 22 which is firmly fixed to the temperature-measuring resistor 21.

The temperature-measuring resistor 21 is configured from a heater having a coil part into which a resistance wire having heat resistance and corrosion resistance is wound in a coil shape.

The temperature-measuring resistor 21 may be formed of, for example, platinum or an alloy thereof.

The gas sensitive part 22 is configured such that an oxidation catalyst is carried by a carrier made of a metal oxide sintered compact.

As examples of the metal oxides constituting the carrier, may be mentioned $ZrO_2$ (zirconia), $Al_2O_3$ (alumina), $SiO_2$ (silica), and zeolite.

As examples of the oxidation catalysts to be used, may be mentioned at least one type selected from the group consisting of Pt, Pd, PtO, $PtO_2$, and PdO.

The content ratio of the oxidation catalyst in the gas sensitive part 22 is, for example, 10 to 30 wt %.

Byway of example, the gas detection elements 20a, 20b may be configured in a manner such that the elemental wire diameter of the resistance wire constituting the temperature-measuring resistor 21 is $\phi$ 0.005 to $\phi$ 0.020 mm, the outer diameter of the coil part is 0.08 to 0.30 mm, the number of times of winding is 6 to 15 turns, and the length of the coil part is 0.10 to 0.40 mm.

The maximum outer diameter D of the gas sensitive part 22 is 0.10 to 0.50 mm, and the length L of the gas sensitive part 22 is 0.10 to 0.50 mm. Furthermore, the closest distance (pitch) p between the gas sensitive part 22 and the lead 16 is 0.10 to 0.50 mm.

Thus, in the contact combustion-type gas sensor 10, the gas inlet of the one detection chamber Sa is provided with a silicone removal filter 25 configured to adsorb and thereby remove a silicone compound. This leads to such an arrangement in which, for example, a common test gas is supplied to the one gas detection element 20a through the silicone removal filter 25 but supplied to the other gas detection element 20b not through the silicone removal filter 25.

For example, the silicone removal filter 25 is preferably employed by allowing a substrate having air permeability such as a pulp sheet to carry silica and being subjected to an adsorption acceleration treatment by iron (III) chloride to accelerate the adsorption of the silicone compound, or by allowing the substrate to carry fumed silica. This makes it possible to avoid the poisoning of the one gas detection element 20a by the silicone compound with reliability and, for example, permit a target gas to be detected such as a paraffinic hydrocarbon gas or hydrogen gas to transmit therethrough. Note that some of target gases being detected, for example, a solvent gas is to be removed by the silicone removal filter 25 because the solvent gas has an adsorption property similar to that of the silicone compound.

For example, such a silicone removal filter 25 may be produced by employing the pulp sheet as a support and impregnating and drying a liquid material. As examples of the liquid materials, may be mentioned a dispersion liquid which is predominantly formed of silica with water as a solvent and contains an iron (III) chloride hydrate. For example, the content ratio of the iron (III) chloride hydrate is 0.3 to 3 wt %. When the fumed silica is used as the silica, the liquid material does not need to include an iron (III) chloride hydrate.

The thickness of the silicone removal filter 25 may be, for example, about 1.0 mm.

The sensor drive unit functions to intermittently drive each of the two gas detection elements 20a, 20b so as to repeat a gas detection cycle that includes the same or continuous energization duration and a non-energization duration for each of the gas detection elements 20a, 20b. As described above, the sensor drive unit may energize each of the two gas detection elements either at the same time or alternately; however, each gas detection element may preferably be intermittently driven so that the two gas detection elements are alternately energized so as to repeat a gas detection cycle Tc that includes the continuous energization durations Te1, Te2 and a non-energization duration Td (see FIG. 1).

As described above, the output processing unit has a gas identification function to identify the type of a target gas being detected in the test gas by contrasting an output variation pattern to a reference output variation pattern acquired in advance, the output variation pattern being constituted by two or more pieces of output data acquired for the test gas by the one gas detection element 20a and two or more pieces of output data acquired for the test gas by the other gas detection element 20b in one gas detection cycle.

For example, if the test gas is a single target gas to be detected that belongs to one of the aforementioned four gas types, the type of the target gas being detected is identified from the aforementioned output variation pattern determination formulas. On the other hand, if the test gas is a mixture of a plurality of target gases to be detected that belong to the same or mutually different gas types or one that is different in the type of base gas from the aforementioned reference gases, the gas type is identified to be "another gas" from the aforementioned output variation pattern determination formulas and outputted to the display unit.

Furthermore, as described above, after identifying the type of the target gas being detected in the test gas, the output processing unit acquires first concentration datum on the basis of the span output value for the reference gas of the identified gas type and the output data acquired to be temporally latest by the one gas detection element 20a in the output variation pattern acquired for the test gas. On the other hand, the output processing unit acquires second concentration datum on the basis of the span output value for the reference gas and the span output value of the output data acquired to be temporally latest by the other gas detection element 20b in the output variation pattern. The output processing unit further has a function to output a value of the higher one of those pieces of data to the display unit as the concentration indication value of the target gas being detected in conjunction with the identified gas type.

Still furthermore, when the output variation pattern acquired for the test gas does not belong to any one of the aforementioned four gas types acquired in advance, the output processing unit outputs the type of the target gas being detected to the display unit as of "another gas." At the same time, the output processing unit acquires first concentration datum on the basis of the output data on the reference gas of a reference output variation pattern that is relatively closer in the variation tendency of the output data to the output variation pattern acquired for the test gas and the output data by the one gas detection element in the output variation pattern acquired for the test gas. Furthermore, the output processing unit acquires second concentration datum on the basis of the output data on the reference gas and the output data by the other gas detection element in the output variation pattern acquired for the test gas. The output processing unit further has a function to output a value of the higher one of those pieces of data to the display unit as another gas concentration indication value.

Further, the aforementioned gas detector is configured to include the silicone removal filter 25 at the gas inlet of one detection chamber Sa in the contact combustion-type gas sensor 10. Thus, according to the aforementioned gas detector, even when used in an environment where a silicone compound or a poisonous substance exists, it is possible to acquire output data with sufficiently high reliability irrespective of the type of the target gas being detected by at least one of the one gas detection element 20a and the other gas detection element 20b. Thus, the gas detector can be configured to have a high durability to silicone poisoning.

Then, the output variation patterns that is constituted by output data groups, say, in one set of two or more pieces of output data acquired by each of the two gas detection elements in one gas detection cycle (four or more pieces of output data in total) are different from each other and unique to the type of the target gas being detected, for example, to each of the four types of the paraffinic hydrocarbon gas, the solvent gas, the hydrogen gas, and the argon gas. Furthermore, even when the gas detection element is poisoned (poisoned with silicone), the output variation pattern of each gas will never be significantly varied.

Thus, according to the aforementioned gas detection method and the gas detector for executing the gas detection method, it is possible to identify the type of a target gas being detected with certain accuracy by contrasting the output variation pattern acquired for the test gas to the reference output variation pattern acquired in advance.

Furthermore, first concentration datum is acquired on the basis of the span output value for the reference gas of the identified gas type and the span output value of the output data acquired to be temporally latest by the one gas detection element 20a in the output variation pattern acquired for the test gas. Second concentration datum is also acquired on the basis of the span output value for the reference gas and the span output value of the output data acquired to be temporally latest by the other gas detection element 20b in the output variation pattern acquired for the test gas. Then, a value of the higher one of those pieces of data is outputted as the concentration indication value of the target gas being detected. This makes it also possible to detect, with certain accuracy, the concentration of the target gas to be detected having an identified type.

Furthermore, since the aforementioned gas detector provides a high durability to silicone poisoning, the amount of the carrier constituting the gas sensitive part of the gas detection element can be reduced as much as possible so as to reduce the size of the gas detection element itself. Thus, since the heat capacity of the gas detection element can be reduced, an additional effect is acquired that the power consumption of the gas detector can be reduced.

Still furthermore, according to the aforementioned gas detector, each of the two gas detection elements 20a, 20b are alternately energized to thereby reduce power consumption. In addition, since the de-energization time of the gas detection elements 20a, 20b is short, it is possible to acquire stable output without a warm-up process of the gas detection elements 20a, 20b for an extended period of time. Furthermore, since only one power source circuit is required to drive the two gas detection elements 20a, 20b, such a configuration as mentioned above makes it possible to reduce the power consumption of the gas detector.

A description will now be given of example experiments that were performed in order to confirm the effects of the present invention.

Example Experiment 1

According to the structure illustrated in FIG. 4 and FIG. 5, a contact combustion-type gas sensor (A) was produced. The specifications of this contact combustion-type gas sensor (A) are shown as below.

<Gas Detection Element>

Temperature-measuring resistor: Material, 10% Rh-90% Pt; Elemental wire diameter, ϕ0.012 mm; Outer diameter of coil part, 0.18 mm; Number of turns, 8 turns; and Length of coil part, 0.20 mm Carrier: Material, Sintered compact of Zirconia (75 wt %) and Alumina (10 wt %)

Oxidation catalyst: Material, Palladium, Content ratio: 14 wt %

Maximum outer diameter D of gas sensitive part: 0.35 mm

Length L of gas sensitive part: 0.35 mm

Closest approach distance between gas sensitive part and lead (pitch) p: 0.3 mm

<Silicone Removal Filter>

Material: Pulp sheet carrying silica and accelerated by iron (III) chloride to adsorb a silicone compound Thickness: about 1 mm A contact combustion-type gas sensor (B) having the same specification as that of the contact combustion-type gas sensor (A) was produced except that a filter including a pulp sheet and hydrophilic fumed silica ("AEROSIL 380" manufactured by Nippon Aerosil Co., Ltd.) carried by the pulp sheet was used as the silicone removal filter.

In each of the contact combustion-type gas sensors (A) and (B), the two gas detection elements were intermittently driven to repeat the gas detection cycles which continuously had the energization duration and the non-energization duration for each of the gas detection elements, and a test gas was acted thereon. Then, in one energization duration of each gas detection element, gas detection signals provided by the gas detection element were sampled, for example, at time intervals of 0.25 seconds to thereby acquire output data from each of the two gas detection elements. Then, the output variation patterns constituted by four pieces of output data for the test gas were acquired for each of the two gas detection elements (eight pieces of output data in total). Here, the applied voltage to the gas detection element was 1.0 V, the energization duration for the gas detection element was one second, and the non-energization duration was 3 seconds. Furthermore, used as the test gas was a methane gas with a concentration of 50% LEL.

The output variation pattern acquired by each of the contact combustion-type gas sensors (A) and (B) shows the tendency that the output values are low at the early stage of the energization duration and the output value rapidly increases at the later stage. Thus, from the aforementioned output variation pattern determination formulas, the test gas is identified to be "a paraffinic hydrocarbon gas."

Furthermore, concentration data was acquired on the basis of the span output value for the reference gas of the identified gas type and the output data by each gas detection element that was acquired to be temporally latest in one energization duration in the acquired output variation pattern. Table 1 below shows the concentration data representing higher values outputted as the concentration indication values of the test gas.

Then, each of the aforementioned contact combustion-type gas sensors (A) and (B) were subjected to a treatment with octamethylcyclotetrasiloxane (D4) with a concentration of 20 ppm for 20 minutes to thereby poison each of the contact combustion-type gas sensors (A) and (B). Then, in the same manner as described above, the output variation pattern of the test gas was acquired. For both the one gas detection element and the other gas detection element, the output variation pattern acquired by each of the contact combustion-type gas sensors (A) and (B) shows the variation tendency that although the magnitudes of the span output values themselves are reduced, the output values are low at the early stage of the energization duration and the output values rapidly increase at the later stage. Thus, it is understood from the aforementioned output variation pattern determination formulas that even after poisoning, the test gas can be identified to be "a paraffinic hydrocarbon gas."

Furthermore, in the same manner as above, the concentration indication value of the test gas was acquired. The results are shown in Table 1 below.

Example Experiment 2

In the same manner as in Example experiment 1 except that isopropyl alcohol (IPA) with a concentration of 50% LEL was used as the test gas, acquired were output variation patterns of the test gas that were constituted by four pieces of output data for each of the two gas detection elements (eight pieces of output data in total). For both the contact combustion-type gas sensors (A) and (B), the acquired output variation pattern according to the one gas detection element shows the tendency that the span output value was substantially "0". Furthermore, for both the contact combustion-type gas sensors (A) and (B), the acquired output variation pattern according to the other gas detection element shows the tendency (mountain type variation tendency) that the span output value increased once with time and then the span output value was reduced with time. Thus, from the aforementioned output variation pattern determination formula, the test gas is identified to be a "solvent gas."

Furthermore, concentration data was acquired on the basis of the span output value for the reference gas of the identified gas type and the output data by each gas detection element that was acquired to be temporally latest in one energization duration in the acquired output variation pattern. Table 1 below shows the concentration data representing higher values outputted as the concentration indication values of the test gas.

Then, after poisoning was performed in the same manner as in Example experiment 1, output variation patterns for the test gas were acquired. For both the contact combustion-type gas sensors (A) and (B), the acquired output variation pattern according to the one gas detection element shows the tendency that the span output value was substantially "0". Furthermore, for both the contact combustion-type gas sensors (A) and (B), the acquired output variation pattern according to the other gas detection element shows the tendency (mountain type variation tendency) that the span output value increased once with time and then the span output value was reduced with time. Thus, from the aforementioned output variation pattern determination formulas, it is understood that the test gas can be identified to be a "solvent gas" even after poisoning.

Furthermore, in the same manner as above, the concentration indication value of the test gas after poisoning was acquired. The results are shown in Table 1 below.

Example Experiment 3

In the same manner as in Example experiment 1 except that a hydrogen gas with a concentration of 50% LEL was used as the test gas, acquired were output variation patterns of the test gas that were constituted by four pieces of output data for each of the two gas detection elements (eight pieces of output data in total). For both the one gas detection element and the other gas detection element, the output variation pattern acquired by each of the contact combustion-type gas sensors (A) and (B) shows the tendency (gradual decrease variation tendency) that the span output values are reduced with time. Thus, from the aforementioned output variation pattern determination formula, the test gas is identified to be a "hydrogen gas."

Furthermore, concentration data was acquired on the basis of the span output value for the reference gas of the identified gas type and the output data by each gas detection element that was acquired to be temporally latest in one energization duration in the acquired output variation pattern. Table 1 below shows the concentration data representing higher values outputted as the concentration indication values of the test gas.

Then, after poisoning was performed in the same manner as in Example experiment 1, output variation patterns for the test gas were acquired. The output variation pattern acquired by each of the contact combustion-type gas sensors (A) and (B) shows the tendency (gradual decrease variation tendency) that the span output values are reduced with time for both the one gas detection element and the other gas detection element. Thus, from the aforementioned output variation pattern determination formulas, it is understood that the test gas can be identified to be a "hydrogen gas" even after poisoning.

Furthermore, in the same manner as above, the concentration indication value of the test gas after poisoning was acquired. The results are shown in Table 1 below.

Example Experiment 4

In the same manner as in Example experiment 1 except that an argon gas with a concentration of 50% LEL was used as the test gas, acquired were output variation patterns of the test gas that were constituted by four pieces of output data for each of the two gas detection elements (eight pieces of output data in total). The output variation pattern acquired by each of the contact combustion-type gas sensors (A) and (B) shows the tendency (gradual increase variation) that the span output values increase with time for both the one gas detection element and the other gas detection element. Thus, from the aforementioned output variation pattern determination formula, the test gas is identified to be an "argon gas."

Furthermore, concentration data was acquired on the basis of the span output value for the reference gas of the identified gas type and the output data by each gas detection element that was acquired to be temporally latest in one energization duration in the acquired output variation pattern. Table 1 below shows the concentration data representing higher values outputted as the concentration indication values of the test gas.

Then, after poisoning was performed in the same manner as in Example experiment 1, output variation patterns for the test gas were acquired. The output variation pattern acquired by each of the contact combustion-type gas sensors (A) and (B) shows the tendency (gradual increase variation) that the span output values increase with time for both the one gas detection element and the other gas detection element.

Thus, from the aforementioned output variation pattern determination formulas, it is understood that the test gas can be identified to be an "argon gas" even after poisoning.

Furthermore, in the same manner as above, the concentration indication value of the test gas after poisoning was acquired. The results are shown in Table 1 of below.

TABLE 1

| | Combution-type Gas Sensor | Test Gas | | Concentration Ingication Value | |
|---|---|---|---|---|---|
| | | Type of Gas | Concentration | Before Poisining | After Poisining |
| Example 1 | Combution-type Gas Sensor (A) | Methane Gas | 50% LEL | 50% LEL | 50% LEL |
| | Combution-type Gas Sensor (B) | | | 50% LEL | 50% LEL |
| Example 2 | Combution-type Gas Sensor (A) | IPA | 50% LEL | 50% LEL | 48% LEL |
| | Combution-type Gas Sensor (B) | | | 50% LEL | 46% LEL |
| Example 3 | Combution-type Gas Sensor (A) | Hydrogen Gas | 50% LEL | 50% LEL | 50% LEL |
| | Combution-type Gas Sensor (B) | | | 50% LEL | 50% LEL |
| Example 4 | Combution-type Gas Sensor (A) | Argon Gas | 50 vol % | 50 vol % | 50 vol % |
| | Combution-type Gas Sensor (B) | | | 50 vol % | 50 vol % |

As is apparent from the results shown in Table 1, even after poisoning, it has been confirmed that the type of a target gas to be detected can be identified with certain accuracy and a target gas to be detected can be detected with certain accuracy irrespective of the gas type.

REFERENCE SIGNS LIST 10 contact combustion-type gas sensor
11 case
12 anti-inflammatory filter
15 base member
16 lead
18 partitioning plate
20a one gas detection element
20b the other gas detection element
21 temperature-measuring resistor
22 gas sensitive part
25 silicone removal filter
Sa one detection chamber
Sb the other detection chamber

The invention claimed is:

1. A gas detection method executed in a gas detector, the gas detector including a contact combustion-type gas sensor in which two gas detection elements that each have a catalyst carried by a carrier made of a metal oxide sintered compact firmly fixed to a temperature-measuring resistor are intermittently driven to repeat a gas detection cycle that includes the same or continuous energization duration and a non-energization duration, the gas detection method comprising:
supplying a reference gas having a known concentration of a target gas to be detected to one gas detection element through a silicone removal filter, and supplying the reference gas to the other gas detection element not through the silicone removal filter so as to acquire, in advance, a reference output variation pattern that is constituted by two or more pieces of output data acquired by the one gas detection element and two or more pieces of output data acquired by the other gas detection element in one gas detection cycle;
acquiring an output variation pattern which is constituted by two or more pieces of output data acquired by the one gas detection element for a test gas and two or more pieces of output data acquired by the other gas detection element for the test gas in one gas detection cycle; and
performing a gas identification process in which the output variation pattern is contrasted to the reference output variation pattern to thereby identify a type of the target gas being detected in the test gas.

2. The gas detection method according to claim 1, wherein in the gas identification process, the type of the target gas being detected in the test gas is identified as any of types of a paraffinic hydrocarbon gas, a solvent gas, a hydrogen gas, and an argon gas.

3. The gas detection method according to claim 1, wherein after the type of the target gas being detected in the test gas is identified in the gas identification process, first concentration datum is acquired on a basis of output data on the reference gas of the identified gas type and output data by the one gas detection element in the output variation pattern acquired for the test gas, and second concentration datum is acquired on a basis of the output data on the reference gas and output data by the other gas detection element in the output variation pattern acquired for the test gas; and a higher one of values represented by the first concentration datum and the second concentration datum is outputted as the concentration indication value of the target gas being detected.

4. The gas detection method according to claim 1, wherein the silicone removal filter of the contact combustion-type gas sensor includes a support having air permeability and silica carried by the support and is further subjected to an adsorption acceleration treatment by iron (III) chloride to accelerate adsorption of a silicone compound.

5. The gas detection method according to claim 1, wherein the silicone removal filter of the contact combustion-type gas sensor includes a support having air permeability, and fumed silica carried by the support.

6. A gas detector comprising:
a contact combustion-type gas sensor, in which two gas detection elements are each disposed in each of two detection chambers that are partitioned from each other, and a gas inlet of one detection chamber is provided with a silicone removal filter, the gas detection elements each having a catalyst carried by a carrier made of a metal oxide sintered compact firmly fixed to a temperature-measuring resistor;
a sensor drive unit configured to intermittently drive each of the two gas detection elements so as to repeat a gas detection cycle that includes the same or continuous energization duration and a non-energization duration for each of the two gas detection elements;
an output processing unit configured to process output data from each of the two gas detection elements; and
a display unit configured to display a type and a concentration of the target gas detected, wherein
the output processing unit has a gas identification function to identify the type of the target gas being detected in the test gas by contrasting an output variation pattern to a reference output variation pattern acquired in advance for a reference gas having a known concentration of the target gas to be detected, the output variation pattern being constituted by two or more pieces of output data acquired by the one gas detection element for the test gas and two or more pieces of output data acquired by the other gas detection element for the test gas in one gas detection cycle.

7. The gas detector according to claim 6, wherein the target gas to be detected which is to be identified is a paraffinic hydrocarbon gas, a solvent gas, a hydrogen gas, and an argon gas.

8. The gas detector according to claim 6, wherein the output processing unit further has a function to acquire, after the type of the target gas being detected in the test gas is identified, first concentration datum on a basis of output data on the reference gas of the identified gas type and output data by the one gas detection element in an output variation pattern acquired for the test gas; to acquire second concentration datum on a basis of output data on the reference gas and output data by the other gas detection element in the output variation pattern acquired for the test gas; and to output a higher one of values represented by the first concentration datum and the second concentration datum as a concentration indication value of the target gas being detected to the display unit in conjunction with the gas type of the target gas being detected.

9. The gas detector according to claim 6, wherein the output processing unit further has a function to output as "another gas" the type of the target gas being detected to the display unit when an output variation pattern acquired for the test gas belongs to none of the target gases to be detected of which patterns were acquired in advance and which are to be identified; to acquire first concentration datum on a basis of output data on a reference gas of a reference output variation pattern of which output data variation tendency is relatively closer to that of an output variation pattern acquired for the test gas and output data by the one gas detection element in an output variation pattern acquired for the test gas; to acquire second concentration datum on a basis of output data on the reference gas and output data by the other gas detection element in the output variation pattern acquired for the test gas; and to output, to the display unit, a higher one of values represented by the first concentration datum and the second concentration datum as the concentration indication value of the another gas.

10. The gas detector according to claim 6, wherein each of the gas detection elements of the contact combustion-type gas sensor employs any of $ZrO_2$ and $Al_2O_3$ as the carrier and at least one type selected from the group consisting of Pt, Pd, PtO, $PtO_2$, and PdO as the catalyst.

11. The gas detector according to claim 6, wherein the silicone removal filter includes a support having air permeability and silica carried by the support and is further subjected to an adsorption acceleration treatment by iron (III) chloride to accelerate adsorption of a silicone compound.

12. The gas detector according to claim 6, wherein the silicone removal filter includes a support having air permeability, and fumed silica carried by the support.

* * * * *